United States Patent
Sudo et al.

[11] Patent Number: 5,984,901
[45] Date of Patent: Nov. 16, 1999

[54] ADAPTER SYSTEM FOR SYRINGE PRE-FILLED WITH LIQUID MEDICAMENT AND SYRINGE PRE-FILLED WITH LIQUID MEDICAMENT

[75] Inventors: Morihiro Sudo; Yasuo Suzuki, both of Tokyo, Japan

[73] Assignee: Daikyo Seiko, Ltd., Tokyo, Japan

[21] Appl. No.: 09/158,613

[22] Filed: Sep. 22, 1998

[30] Foreign Application Priority Data

Feb. 16, 1998 [JP] Japan ................... 10-032858

[51] Int. Cl.⁶ ...................................... A61M 5/00
[52] U.S. Cl. ............................................ 604/227
[58] Field of Search ............... 604/227, 187, 604/232, 189

[56] References Cited

U.S. PATENT DOCUMENTS

| | | | |
|---|---|---|---|
| 2,410,351 | 10/1946 | Lockhart | 604/232 X |
| 2,854,975 | 10/1958 | Cohen | 604/227 |
| 4,484,915 | 11/1984 | Tartaglia | 604/227 |
| 4,909,788 | 3/1990 | Egolf | 604/227 X |
| 5,419,775 | 5/1995 | Haffner et al. | 604/227 |
| 5,692,640 | 12/1997 | Caulfield et al. | 604/189 X |

*Primary Examiner*—John D Yasko
*Attorney, Agent, or Firm*—McCormick, Paulding & Huber LLP

[57] ABSTRACT

An adaptor system includes a plastic syringe which is pre-filled with a liquid medicament, and a plastic flange adaptor which can be attached to the syringe. The medicament-prefilled syringe is provided with a cylindrical body having a small diameter cylindrical body to which a liquid medicament information label is adhered and a large diameter cylindrical body, and an end flange. The flange adaptor is provided with a cylindrical base portion having an insertion hole whose diameter is such that the inner wall of the insertion hole does not contact the small diameter cylindrical body of the syringe and is in contact with the large diameter cylindrical body when the flange adaptor is fitted to the syringe, and a large diameter flange portion which surrounds the end flange of the syringe. The invention is also directed to a medicament-prefilled plastic syringe itself.

6 Claims, 2 Drawing Sheets

ADAPTER SYSTEM FOR SYRINGE PRE-FILLED WITH LIQUID MEDICAMENT AND SYRINGE PRE-FILLED WITH LIQUID MEDICAMENT

BACKGROUND OF THE INVENTION

1. Field of the Invention

The present invention relates to a plastic syringe which is provided at its rear end with a flange and which is pre-filled with a liquid medicament, and an adaptor system composed of such a medicament-prefilled syringe and a plastic flange adaptor which is attached to the flange of the plastic syringe.

2. Description of the Related Art

In a known medicament-prefilled syringe system, a syringe which has been filled with a liquid medicament is prepared and is adapted, upon dosage, to inject the liquid medicament contained in the syringe into a patient's body by moving the plunger of the syringe. In this medicament-prefilled syringe system, the syringe is provided, on the outer peripheral surface thereof, with a label which bears information including the name and/or ingredients of the liquid medicament contained in the syringe.

Upon injection of the liquid medicament from the syringe, in general, an operator moves the plunger using his or her thumb while holding the flange provided at the rear end of a cylinder of the syringe with the operator's index finger and middle finger. However, the flange at the rear end of the syringe is so small that it is difficult for the operator to carry out a smooth injection depending on the viscosity of the liquid medicament or the external force exerted on the plunger by the operator. To solve this problem, an additional flange adaptor whose diameter is larger than that of the rear flange of the syringe is attached to the flange at the rear end of the cylinder of the syringe according to need. To attach the flange adaptor, the syringe is inserted in the flange adaptor, with the end of the syringe that is located away from the flange being the leading end. When the larger flange adaptor is attached to the syringe, the flange adaptor abuts against the flange of the syringe, so that the diameter of the flange is substantially increased.

In order to give a secure feeling of the adapter being in place and a secure feeling thereof when in use, it is preferable that the flange adaptor be firmly fitted onto the outer peripheral surface of the cylinder of the syringe or be in close contact with the rear flange of the syringe. However, if the flange adaptor is firmly fitted onto the outer peripheral surface of the syringe body, the label provided on the outer peripheral surface of the syringe body can easily be rubbed by the flange adaptor upon attachment thereof, so that the label may possibly get separated or damaged. If separation or damage of the label occurs, there is a danger of the operator not being able to identify the liquid medicament contained in the syringe.

SUMMARY OF THE INVENTION

It is an object of the present invention to provide an adaptor system composed of a medicament-prefilled syringe and a flange adaptor, wherein the flange adaptor can be firmly attached to the syringe without danger of separation or breakage of the label adhered to the outer peripheral surface of the syringe body, giving a secure feeling of the adapter being in place and a secure feeling thereof when in use.

To achieve the object mentioned above, according to the present invention, there is provided an adaptor system including a plastic syringe which is pre-filled with a liquid medicament, and a plastic flange adaptor which can be attached to the syringe. The medicament-prefilled syringe includes a nozzle, a cylindrical body and an end flange in that order. The cylindrical body constitutes a small diameter cylindrical body adjacent to the nozzle and a large diameter cylindrical body adjacent to the end flange wherein the large diameter cylindrical body has a larger diameter than the small diameter cylindrical body. The flange adaptor constitutes a cylindrical base portion having an insertion hole whose diameter is such that the inner wall of the insertion hole does not make contact with the small diameter cylindrical body of said syringe and is in contact with the large diameter cylindrical body when the flange adaptor is inserted into the syringe; and a large diameter flange portion which surrounds the end flange of the syringe.

Preferably, the syringe is provided, on the outer peripheral surface of the small diameter cylindrical body, with a label which bears information on the liquid medicament contained in the syringe, so that the inner diameter of the insertion hole of the cylindrical base portion of the flange adaptor is such that contact of the inner wall of the insertion hole with the label does not occur when the flange adaptor is fitted to the syringe.

Preferably, the following condition is satisfied: $D-d \leq 0.1$ mm; wherein "D" represents the nominal inner diameter of the insertion hole of the cylindrical base portion of the flange adaptor and "d" represents the nominal outer diameter of the small diameter cylindrical body of the syringe, respectively.

Preferably, the flange adaptor is provided with an engagement recess in which the end flange of the syringe can be fitted.

According to another aspect of the present invention, there is provided a medicament-prefilled plastic syringe constituting a cylindrical body which is filled with a liquid medicament, and a nozzle and an end flange formed at the front and rear ends of the cylindrical body thereof. The cylindrical body includes a small diameter cylindrical body adjacent to the nozzle and a large diameter cylindrical body adjacent to the end flange; the large diameter cylindrical body has a larger diameter than the small diameter cylindrical body.

Preferably, the syringe is provided, on the outer peripheral surface of the small diameter cylindrical body, with a label which bears information on the liquid medicament contained in the syringe.

The present disclosure relates to subject matter contained in Japanese Patent Application No. 10-32858 (filed on Feb. 16, 1998) which is expressly incorporated herein by reference in its entirety.

BRIEF DESCRIPTION OF THE DRAWINGS

The invention will be discussed below in detail with reference to the accompanying drawings, in which.

DESCRIPTION OF THE PREFERRED EMBODIMENT

Figure 1:
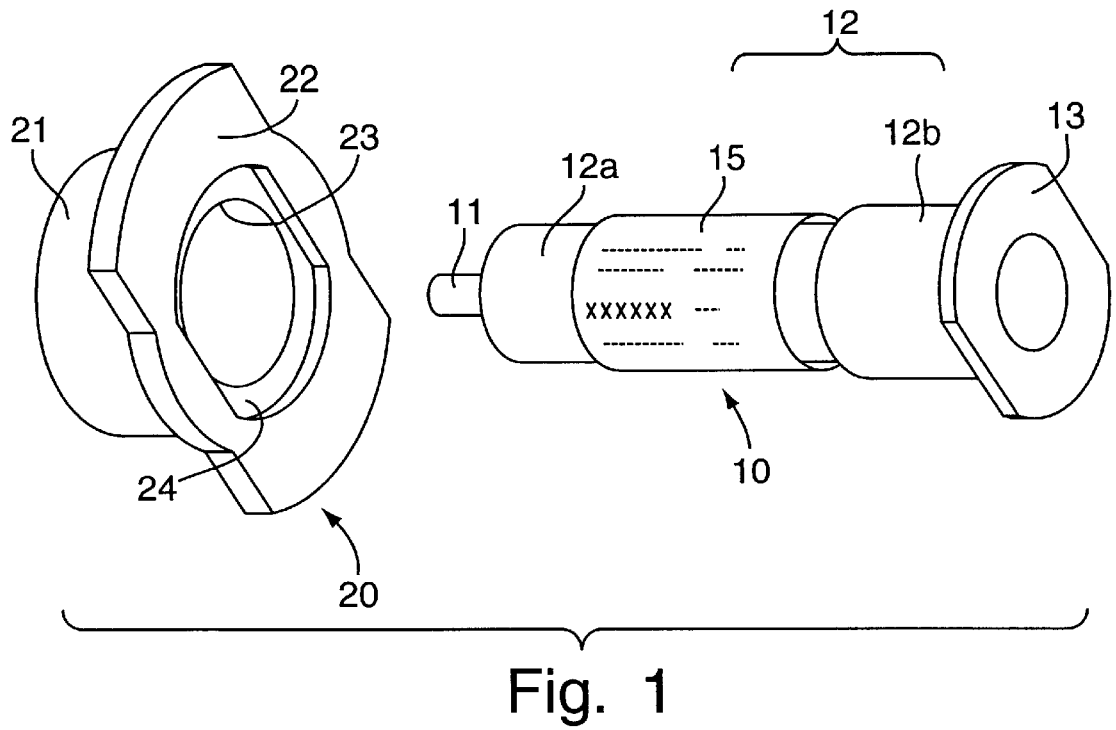
FIG. 1 is an exploded perspective view of a syringe and a flange adaptor in an adaptor system for a medicament-prefilled syringe according to the present invention.

A syringe 10 having a liquid medicament pre-filled therein is made of synthetic resin and is composed of a nozzle 11, a cylindrical body 12 and a flange 13 in this order from the front end. The cylindrical body 12 includes a outside diameter cylindrical body 12a adjacent to the nozzle 11 and a stepped large outside diameter cylindrical body 12b adjacent to the flange 13. The small outsidel diameter portion 12a is provided on the outer peripheral surface thereof with a label 15 adhered thereto, which bears information on the liquid medicament contained in the syringe. The outer diameter D of the large outside diameter cylindrical body 12b is greater than the diameter d of the small outside diameter cylindrical body 12a including the label 15. The small outside diameter body 12a and the large outside diameter body 12b form a common interior chamber 13 of uniform diameter for receiving the medicament and for cooperation with the plunger for expressing the medicament from the chamber through the nozzle 12. Note that the plunger for the syringe is not shown in the drawings; the seal mechanism of the syringe to prevent leakage of the liquid medicament contained in the syringe 10 is not the subject of the present invention.

A flange adaptor 20 which can be attached to the medicament-prefilled syringe 10 is made of synthetic resin and is composed of a cylindrical body 21 which can be attached to the large diameter cylindrical body (stepped portion) 12b and a large diameter flange portion 22 provided at one end of the cylindrical body 21. The axial length of the cylindrical body 21 is substantially identical to the axial length of the large diameter cylindrical body 12b of the syringe body 10. The cylindrical body 21 defines therein an insertion hole 23 whose nominal inner diameter D is greater than the nominal outer diameter d of the small diameter cylindrical body 12a of the syringe body 10 and is substantially equal to the nominal diameter D of the large diameter cylindrical body 12b. In practice, the diameter of the insertion hole 23 of the flange adaptor 20 is determined taking into account the thickness of the label 15, so that the label 15 is not damaged by the flange adaptor 20 when the cylindrical body 21 of the flange adaptor 20 is fitted to the syringe. For example, if the thickness of the label 15 is equal to or smaller than 0.05 mm, the difference in the diameter between the insertion hole 23 and the small outside diameter cylindrical body 12a of the syringe body satisfies the following condition: $D-d \leq 0.1$ mm.

The large diameter flange portion 22 includes a recess 24 formed around the insertion hole 23, for receiving the end flange 13 of the syringe body 10. The shape of the recess 24 in a front elevational view is equivalent to the shape of the end flange 13 of the syringe body 10. The depth of the recess 24 in the axial direction is equivalent to the thickness of the end flange 13. The shape of the large diameter flange portion 22 in a front elevational view is analogous to and sufficiently greater than the shape of the end flange 13. Accordingly, the end flange of the syringe can be substantially enlarged.

Figure 3:
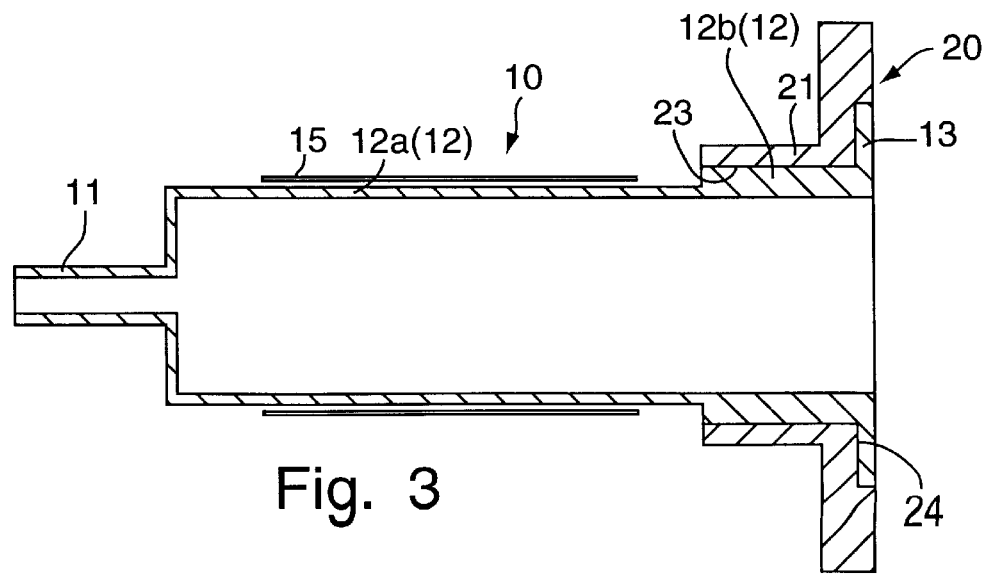
FIG. 3 is a sectional view of the syringe and flange adaptor attached thereto shown in FIG. 1.
Figure 2:
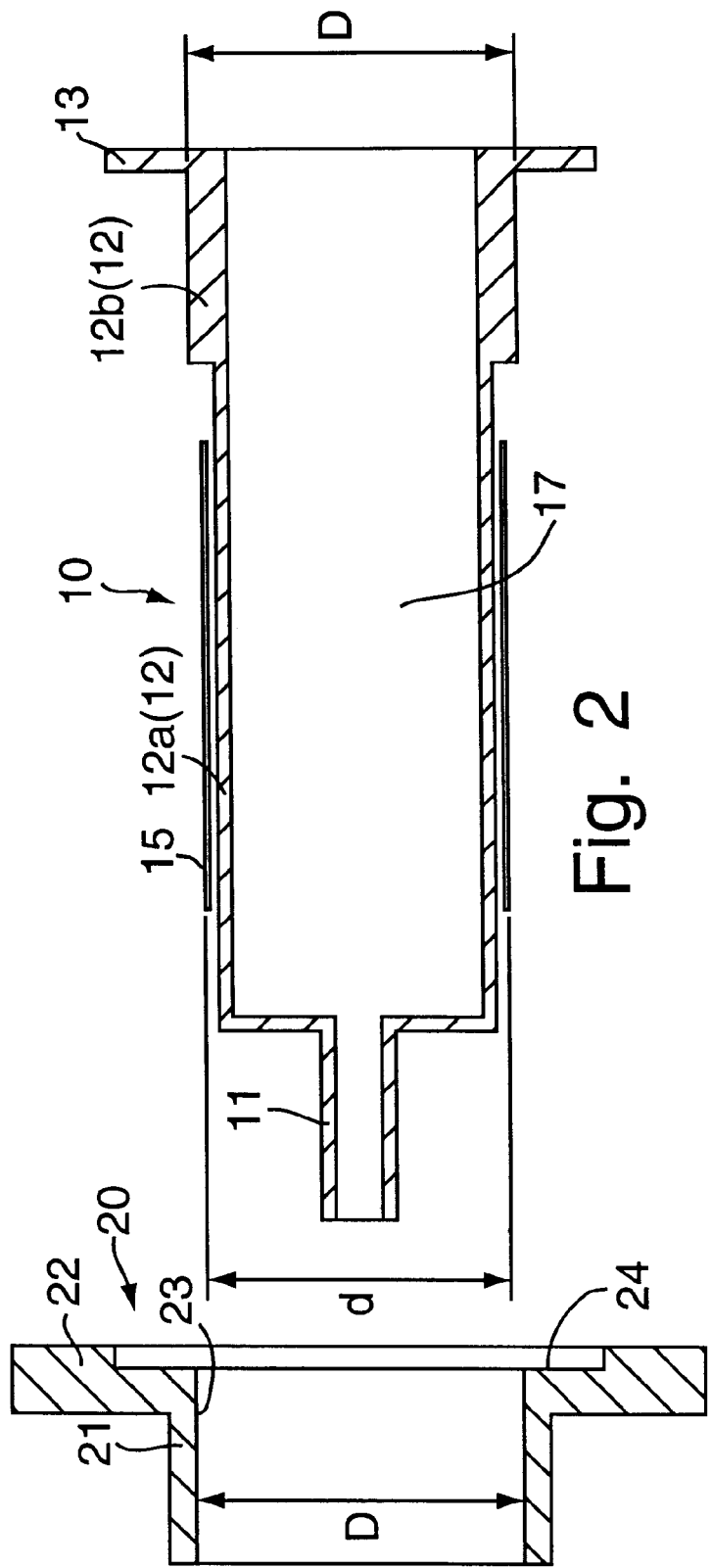
FIG. 2 is a sectional view of the syringe and flange adaptor shown in FIG. 1.

In the adaptor system for the medicament-prefilled syringe constructed as described above, the flange adaptor 20 is fitted onto the syringe 10 from the front end of the syringe body 10. Namely, the cylindrical body 12 of the syringe 10 is inserted in the insertion hole 23 of the cylindrical body 21 of the flange adaptor 20 and thereafter the flange adaptor 20 is relatively moved toward the end flange 13. During the relative movement of the flange adaptor 20, the label 15 is not rubbed by the inner wall of the insertion hole 23 since the inner diameter D of the insertion hole 23 is larger than the outside diameter d of the small outside diameter cylindrical body 12a of the syringe 10. When the insertion hole 23 is moved to the large outside diameter cylindrical body 12b, the insertion hole 23 is firmly fitted onto the large outside diameter cylindrical body 12b, and the end flange 13 of the syringe 10 is firmly fitted into the recess 24 of the flange adaptor 20 (FIG. 3).

In this state, the cylindrical body 21 (insertion hole 23) of the flange adaptor 20 is fitted on the large diameter cylindrical body (stepped portion) 12b, and the flange portion 13 is firmly fitted into the recess 24. Consequently, no play between the flange adaptor 20 relative to the syringe 10 can occur. Thus, giving a secure feeling of the adapter being in place, a secure feeling thereof when in use, and the label 15 adhered to the peripheral surface of the small outside diameter cylindrical body 12a of the syringe is not damaged.

It is not always necessary for the shape of the recess 24 of the flange adaptor 20 to be exactly the same as the shape of the flange 13, so long as the recess 24 can receive the end flange 13 of the syringe 10. It is preferable that the depth of the recess 24 be equal to the thickness of the end flange 13, so that when the flange 13 is fitted in the recess 24, the flange 13 is flush with the surface of the flange portion 22.

Although the illustrated embodiment is applied to an adaptor system constituting of a syringe 10 and a flange adaptor 20 in combination, it is possible to fit the syringe 10 to an existing flange adaptor, so that the large diameter cylindrical body 12b of the syringe 10 is connected to the cylindrical portion of an existing flange adaptor. Namely, the subject of the present invention can be also addressed to a medicament-prefilled syringe without a flange adaptor.

As can be understood from the above discussion, according to the present invention, in a system in which an enlarged flange adaptor is attached to a rear flange of a plastic syringe which has been filled with a liquid medicament to obtain a large diameter flange, no separation or breakage of a label adhered to the peripheral surface of the syringe by the flange adaptor occurs when the flange adaptor is attached to the syringe. Moreover, a secure feeling of the adapter being in place and a secure feeling thereof when in use can be obtained. In addition to the foregoing, according to the present invention, if the medicament-prefilled plastic syringe is used with an existing flange adaptor, wherein the stepped portion of large outside diameter is fitted in the cylindrical body of the existing flange adaptor, the same operation and technical advantages as those expected from a combination of the medicament-prefilled syringe and the flange adaptor according to the present invention can be obtained.

What is claimed is:

1. An adaptor system comprised of a plastic syringe which is pre-filled with a liquid medicament, and a plastic flange adaptor which can be attached to said syringe; wherein said medicament-prefilled syringe comprises a nozzle, a cylindrical body and an end flange in this order; said cylindrical body comprising a small outside diameter cylindrical body adjacent to said nozzle and a large outside diameter cylindrical body adjacent to said end flange; said large outside diameter cylindrical body having a larger outside diameter than said small outside diameter cylindrical body and said small outside diameter body and said large outside diameter body together forming a common interior cylindrical chamber of uniform diameter; and wherein said flange adaptor comprises: a cylindrical base portion having an insertion hole whose diameter is such that the inner wall of the insertion hole does not make contact with said small outside diameter cylindrical body of said syringe and is in contact with said large outside diameter cylindrical body when said flange adaptor is inserted onto said syringe; and a large diameter flange portion which surrounds said end flange of said syringe when said flange adaptor is inserted onto said syringe.

2. An adaptor system for a medicament-prefilled syringe according to claim 1, wherein said syringe is provided, on the outer peripheral surface of the small diameter cylindrical body, with a label which bears information on the liquid medicament contained in said syringe, so that the inner diameter of said insertion hole of said cylindrical base portion of said flange adaptor is such that contact of the inner wall of said insertion hole with said label does not occur when the flange adaptor is fitted to said syringe.

3. An adaptor system for a medicament-prefilled syringe according to claim 1, wherein the following condition is satisfied:

$D-d \leqq 0.1$ mm;

wherein "D" represents the nominal inner diameter of said insertion hole of said cylindrical base portion of said flange adaptor and "d" represents the nominal outside diameter of said small outside diameter cylindrical body of said syringe, respectively.

4. An adaptor system for a medicament-prefilled syringe according to claim 1, wherein said flange adaptor is provided an engagement recess in which said end flange of said syringe can be fitted.

5. A medicament-prefilled plastic syringe comprising: a cylindrical body which is filled with a liquid medicament, and a nozzle and an end flange formed respectively at the front and rear ends of said cylindrical body thereof; wherein said cylindrical body comprises a small outside diameter cylindrical body adjacent to said nozzle and a large outside diameter cylindrical body adjacent to said end flange; said large outside diameter cylindrical body having a larger diameter than said small outside diameter cylindrical body and said small outside diameter body and said large outside diameter body together forming a common interior cylindrical chamber of uniform diameter.

6. A medicament-prefilled plastic syringe according to claim 5, wherein said syringe is provided, on the outer peripheral surface of the small outside diameter cylindrical body, with a label which bears information on the liquid medicament contained in said syringe.

* * * * *